United States Patent [19]

Layman-Spillar et al.

[11] Patent Number: 5,554,106
[45] Date of Patent: Sep. 10, 1996

[54] HYDROCOLLOID EXIT SITE DRESSING

[75] Inventors: Lynn M. Layman-Spillar, Seattle; Margo L. Gisselberg, Lynnwood; Bradford C. Fowler, Woodinville, all of Wash.

[73] Assignee: Quinton Instrument Company, Bothell, Wash.

[21] Appl. No.: 322,894

[22] Filed: Oct. 13, 1994

[51] Int. Cl.$^6$ ...................... A61F 13/00
[52] U.S. Cl. .............. 602/42; 602/41; 604/175; 128/DIG. 26
[58] Field of Search .................. 604/174, 175; 602/41, 45, 46; 128/DIG. 26

[56] References Cited

U.S. PATENT DOCUMENTS

| | | | |
|---|---|---|---|
| 802,190 | 10/1905 | Heineman. | |
| 2,169,947 | 8/1939 | Freudenberg | 128/156 |
| 2,492,458 | 12/1949 | Bering, Jr. | 167/74 |
| 2,533,004 | 12/1950 | Ferry et al. | 260/112 |
| 2,814,294 | 11/1957 | Figge | 128/215 |
| 3,728,207 | 4/1973 | Heling | 161/151 |
| 3,800,792 | 4/1974 | McKnight et al. | 128/156 |
| 3,903,882 | 9/1975 | Augurt | 128/155 |
| 3,972,328 | 8/1976 | Chen | 602/42 |
| 4,016,877 | 4/1977 | Cruz, Jr. et al. | 128/156 |
| 4,060,081 | 11/1977 | Yannas et al. | 128/156 |
| 4,066,083 | 1/1978 | Ries | 128/325 |
| 4,080,970 | 3/1978 | Miller | 604/174 |
| 4,148,664 | 4/1979 | Cruz, Jr. | 106/161 |
| 4,167,945 | 9/1979 | Gottlieb | 128/334 |
| 4,191,751 | 3/1980 | Gottlieb | 424/177 |
| 4,215,686 | 8/1980 | Gregory et al. | 128/256 |
| 4,238,480 | 12/1980 | Sawyer | 424/177 |
| 4,290,519 | 9/1981 | Harvey | 198/483 |
| 4,327,722 | 5/1982 | Groshong et al. | 128/214.4 |
| 4,341,207 | 7/1982 | Steer et al. | 128/155 |
| 4,347,841 | 9/1982 | Benyo et al. | 128/156 |
| 4,390,519 | 6/1983 | Sawyer | 424/28 |
| 4,393,080 | 7/1983 | Pawelchak et al. | 428/355 |
| 4,404,970 | 9/1983 | Sawyer | 128/325 |
| 4,407,787 | 10/1983 | Stemberger | 424/28 |
| 4,516,968 | 5/1985 | Marshall | 604/174 |
| 4,570,629 | 2/1986 | Widra | 128/156 |
| 4,576,817 | 3/1986 | Montgomery et al. | 424/94 |
| 4,578,067 | 3/1986 | Cruz, Jr. | 604/368 |
| 4,606,910 | 8/1986 | Sawyer | 424/28 |
| 4,614,794 | 9/1986 | Easton et al. | 530/356 |

(List continued on next page.)

FOREIGN PATENT DOCUMENTS

| | | | |
|---|---|---|---|
| 2057269 | 4/1981 | United Kingdom | 604/174 |
| 9307928 | 4/1993 | WIPO. | |

OTHER PUBLICATIONS

12 R. Bhatnagar and A. Ray, *Composites of Collagen with Synthetic Polymers for Biomedical Applications*, Advanced Concepts, pp. 179–184.

K. Hoyman, S. Griffin and D. Drew, *Hydrocolloid Wafer Dressings and Atrial Catheter Access Sites*, Ostomy/Wound Management, Spring 1989, pp. 22–27.

Advertisement for BIOPATCH Antimicrobial Dressing by Johnson & Johnson Medical Inc., *Critical Care Nurse*, Feb. 1994.

*Primary Examiner*—Randall L. Green
*Assistant Examiner*—Chalin Smith
*Attorney, Agent, or Firm*—Montgomery W. Smith; Richard D. Allison

[57] ABSTRACT

A dressing is described which is preferably constructed of a layer of hydrocolloid material having a downwardly extending lip member thereon that is sized to be received adjacent to a percutaneous device which is at least partially implanted into a patient such that the dressing having a lip member thereon forms a physical barrier to decrease the incidence of catheter tract infections in a patient and the lip member provides a downward extension into the wound to help remove exudate and detritus from the catheter tract and wherein the dressing further includes a mesh layer adjacent to the skin of the patient to minimize the amount of hydrocolloid material remaining on the skin of the patient after use.

33 Claims, 6 Drawing Sheets

U.S. PATENT DOCUMENTS

| | | | |
|---|---|---|---|
| 4,655,210 | 4/1987 | Edenbaum | 602/46 |
| 4,655,211 | 4/1987 | Sakamoto et al. | 128/156 |
| 4,676,782 | 6/1987 | Yamamoto et al. | 604/175 |
| 4,725,671 | 2/1988 | Chu et al. | 530/356 |
| 4,775,585 | 10/1988 | Hagiwara et al. | 428/323 |
| 4,784,653 | 11/1988 | Bolton et al. | 604/307 |
| 4,789,401 | 12/1988 | Ebinger et al. | 106/122 |
| 4,841,962 | 6/1989 | Berg et al. | 128/156 |
| 4,847,049 | 7/1989 | Yamamoto | 422/24 |
| 4,856,504 | 8/1989 | Yamamoto et al. | 128/92 |
| 4,867,748 | 9/1989 | Samuelsen | 604/336 |
| 4,897,081 | 1/1990 | Poirier et al. | 604/175 |
| 4,911,898 | 3/1990 | Hagiwara et al. | 423/118 |
| 4,915,694 | 4/1990 | Yamamoto et al. | 604/180 |
| 4,925,924 | 5/1990 | Silver et al. | 530/356 |
| 5,060,642 | 10/1991 | Gilman | 128/155 |
| 5,085,646 | 2/1992 | Svenson | 604/175 |
| 5,098,397 | 3/1992 | Svensson | 604/174 |
| 5,156,592 | 10/1992 | Martin et al. | 604/43 |
| 5,213,567 | 5/1993 | Masaki | 604/19 |
| 5,236,421 | 8/1993 | Becher | 604/180 |
| 5,242,415 | 9/1993 | Kantrowitz | 604/175 |
| 5,264,218 | 11/1993 | Rogozinski | 602/41 |
| 5,308,313 | 5/1994 | Karami et al. | 602/55 |
| 5,364,367 | 11/1994 | Banks | 604/174 |

HYDROCOLLOID EXIT SITE DRESSING

BACKGROUND OF THE INVENTION

The present invention relates to an improved dressing for use with percutaneous devices or catheters and more particularly with long term or other vascular access catheters, such as hemodialysis catheters. In a preferred form of the present invention, the dressing includes a portion thereof which extends into the catheter tract a short distance along the shaft of the catheter. The present invention may also include various layers, such as, a thin film or a mesh layer along the surface of the dressing which is adjacent to the skin of the patient.

The use of percutaneous devices, including long term or vascular access catheters has steadily increased in recent years. For example, various right atrial catheters or medication ports may be surgically placed in the patient and are intended to remain in the patient indefinitely. This use of relatively long term catheters or access devices may eliminate or minimize the need for multiple punctures of the blood vessels of the patient to obtain blood samples or to administer medications by providing prolonged access to the blood vessels of the patient. With these types of catheters, medical personnel are provided with convenient access to the blood vessels of the patient without concern for rotating IV sites or frequently re-establishing large vein access.

The increased use of the longer term catheters has also brought difficulties not typically encountered. Infections or various forms of skin irritation around the catheter or access site have now become a more common occurrence. The dressings used with short term catheters are typically either gauze and tape or transparent film dressings, depending on the preference of the clinician and/or the patient. With the shorter term catheters, infections are usually not a major concern because the catheter is in place for a relatively short period of time and it is not necessary to repeatedly change the dressing. Despite this, the occurrence of exit site infections, catheter tract infections and septicemia has been reported. The most common occurrence encountered with these dressings are an allergic reaction to the material or adhesive.

The area where the catheter or other percutaneous device enters or exits the skin of the patient is known as the exit site and is particularly sensitive to infections or irritation because it is essentially an open wound. As used herein, exit site is intended to refer to the area along the skin of the patient which is adjacent to the percutaneous device. The area beneath the skin of the patient along the shaft of the catheter or other percutaneous device is referred to herein as the catheter tract. Many of the currently available dressings are used to protect the patient from infections at the exit site and in the catheter tract by providing a physical barrier which prevents the infiltration of bacteria, debris or detritus into the body of the patient.

Under normal conditions, the inflammatory phase of the wound healing response will remove the cellular detritus or exudate and bacteria from the catheter tract or exit site. It is believed that the presence of the bacteria in the catheter tract or exit site in addition to the detritus or exudate may be a cause of exit site or catheter tract infections. Over an extended period of time, cellular turnover in the catheter tract may result in a buildup of cellular detritus or exudate along the shaft of the catheter or along a cuff on the catheter as described more fully below. The detritus is usually removed by phagocytic cells as part of the overall inflammatory response around an implanted device unless the rate of detritus or exudate formation exceeds the capacity for removal by the phagocytic cells. The detritus or exudate may also accumulate within small pores in the cuff which may be inaccessible to the phagocytic cells. If bacteria is also present in the cuff, an infection may then develop in the catheter tract. Additionally, the movement of the shaft of the catheter in the catheter tract caused by normal movement of the patient or dressing changes and also the initial tunneling or incision which is used for the original catheter placement may similarly increase the presence of detritus and bacteria in the catheter tract. Furthermore, the phagocytic activity of the phagocytic cells in immunocompromised patients, such as hemodialysis or chemotherapy patients, is significantly reduced. Therefore, because of the increased presence of detritus and bacteria in the catheter tract of the same patients that typically use longer term catheters, the normal reparative phase of wound repair either takes longer than in normal situations or does not occur at all.

Another factor which potentially contributes to the increasing incidence of catheter tract infections is the fact that many dressings must be changed at least daily or on a regular basis. The increased handling of the catheter during each dressing change may increase the movement of the catheter in the catheter tract. Additionally, the skin of the patient around the exit site is irritated because of the adhesives or other materials which are used to clean the skin and adhere the dressing to the skin of the patient.

One approach that is commonly used to reduce the likelihood of catheter tract infections is to use a cuff which is constructed of a felt or similar material on the portion of the catheter which is placed subcutaneously. These cuffs typically include a material which is designed to allow tissue ingrowth into the cuff to form a physical barrier which inhibits migration of bacteria along the catheter tract below the cuff. It is believed that the effectiveness of various cuffs may be adversely affected by the amount of debris or bacteria which works its way down the catheter tract from the exit site. Although studies have shown that the use of cuffs may decrease the likelihood of catheter tract infections during the use of longer term catheters, the tissue surrounding the catheter tract and the cuff requires a debris and bacteria free area for the optimal functioning of the cuff so that the tissue is able to satisfactorily grow into or infiltrate the cuff.

One current approach to reducing the incidence of exit site or catheter tract infections is for newly implanted or injured catheter exit sites to be wrapped with a square cotton gauze pad and the catheter and gauze pad are then sandwiched between two semipermeable polyurethane transparent films. The advantage in using a transparent film in this type of arrangement is that the film stabilizes the catheter, conforms easily to the skin and forms a physical bacterial barrier on the skin of the patient. The gauze in this type of dressing arrangement absorbs the exudate from the exit site. A disadvantage of this arrangement is that it is time consuming to apply the dressing to the patient and the transparent film is typically one-way permeable so that the skin of the patient remains dry while moisture is allowed to evaporate. This may increase the scarring along the exit site. Furthermore, this type of dressing does not remove cellular debris or bacteria in the exit site or along the catheter tract and the bacteria or tissue debris may build up along the shaft of the catheter or along a felt-type cuff as described below.

More recently, a number of studies have been performed using hydrocolloid dressings in an effort to improve exit site care and reduce the skin irritation which may occur with various other types of dressings. The hydrocolloid dressings include moisture reactive particles embedded in a polymer base. The moisture reactive particles are believed to react with the wound exudate and form a soft gel over the wound to actively remove bacteria and wound exudate from the exit site or catheter tract while protecting the newly formed tissue during the removal of the dressing. The idea of using hydrocolloid dressings is particularly attractive with longer term catheters because the hydrocolloid material provides a moist wound healing environment which encourages faster healing and less scarring around the exit site. Additionally, the hydrocolloid material forms a physical barrier on the skin to block the migration of bacteria into the catheter tract. The hydrocolloid material also creates a slightly acidic environment underneath the dressing which inhibits microbial growth.

Although the hydrocolloid type dressings have been shown to form an effective bacterial barrier on the skin of the patient, this type of dressing has a tendency to "melt" onto the skin of the patient as the wound exudate or other moisture is absorbed by the dressing. When the user attempts to remove the dressing from the exit site, some of the melted hydrocolloid material may continue to adhere to the exit site and the shaft of the catheter. This is considered to be undesirable because of the extra time necessary for the clinician to remove the hydrocolloid material that adheres to the exit site, catheter tract and the shaft of the catheter after the dressing is removed as well as the resulting damage caused to the newly formed epithelium by removal of the hydrocolloid material therefrom. Therefore, even though the hydrocolloid dressings provide an acceptable barrier and also promote healing of the wound, the need to remove portions of the hydrocolloid material after the dressing has been removed from the skin of the patient has limited the acceptance of this type of dressing for use with longer term catheters or similar devices.

Therefore, there is a need for a dressing which will inhibit or reduce the incidence of infections at the exit site and along the catheter tract so that the likelihood that the tissue will grow into the cuff is maximized.

There is a further need for a dressing that will easily fit around the catheter and which will protect and conform to the exit site. Additionally, a preferred form of the dressing of the present invention includes a portion thereof which extends into the catheter tract and assists in the removal of bacteria and debris therefrom while forming a physical barrier along a portion of the catheter shaft.

SUMMARY OF THE INVENTION

It is an object of the present invention to provide a dressing which is easy to apply around the catheter and onto the exit site.

It is a further object of the present invention to provide a dressing which provides a physical and/or bacterial barrier around the surface of the skin of the patient and which protects the catheter tract from the migration or accumulation of bacteria and detritus from the skin adjacent to the exit site along the shaft of the catheter.

It is yet another object of the present invention to provide a dressing having a film and/or a mesh layer thereon to facilitate the adherence of the dressing to the skin of the patient and the removal therefrom after use.

It is yet another object of the present invention to provide a dressing which includes one or more tab members thereon to further facilitate the removal of the dressing from the skin of the patient.

In one form of the present invention, the dressing is preferably formed of a layer of hydrocolloid material. The dressing may be cut into nearly any desired shape and includes a generally flat top surface and a bottom surface which preferably includes a generally downwardly extending ridge-like lip surface thereon. The ridge-like lip surface is shaped to conform to the exit site and a portion of the catheter tract of the patient such that a portion of the dressing extends a short distance into the subcutaneous tissue along the catheter tract in the patient to cushion the exit site from the movement of the catheter shaft, to prevent bacteria or debris from entering the exit site and also to remove debris or bacteria from the exit site. The ridge-like lip surface surrounds a generally oval or circular shaped opening in the dressing which is sized to receive the catheter therein. Additionally the dressing preferably includes a slit therein which extends between the opening in the dressing and the periphery thereof.

In another form of the present invention, the dressing is formed of a plurality of layers. In a preferred form of this invention, the dressing includes a top layer formed of a film-like material such as a polyurethane which covers a middle layer that is formed of a foam-like material. The bottom layer is preferably formed of a moisture reactive material, such as a hydrocolloid material which also preferably includes the ridge-like lip surface extending downwardly therefrom around the generally centrally located opening in the dressing.

In yet another preferred form of the present invention, the dressing includes a mesh-like material incorporated into the bottom surface of the dressing. The mesh-like material surface is also preferably incorporated into the portion of the dressing which surrounds the generally centralized opening in the dressing to assist in the removal of the ridge like portion of the dressing from the skin and exit site of the patient after use. In a further modification of this form of the invention, the mesh-like material may be positioned along the bottom surface of the dressing and along the ridge-like lip surface, if present. Alternately, a layer of film-like material may extend along the top surface of the dressing and along the portion of the ridge-like lip surface of the dressing adjacent to the shaft of the catheter.

In yet another form of the present invention, the dressing may include one or more tab members along the slit to facilitate the application and removal of the dressing from the skin of the patient.

An advantage of the dressing of the present invention is that the dressing is easy to manufacture and use.

Another advantage of the present invention is that the dressing may reduce the likelihood of exit site and catheter tract infections with regular and proper use.

Yet another advantage of the present invention is that the use of the mesh-like material and the tab members facilitate the removal of the dressing from the skin of the patient while minimizing the residue of the hydrocolloid material remaining on the skin of the patient after use.

A further advantage of the dressing of the present invention is that the dressing may be adapted for use with nearly any catheter or other vascular or non-vascular percutaneous device.

DETAILED DESCRIPTION OF THE PREFERRED EMBODIMENTS

As shown in FIGS. 1–4, a preferred form of the present invention includes a dressing which is referred to hereinafter generally as dressing 10. The dressing 10 preferably includes a central opening 12 formed therein and an elongate slit 14 which extends between the periphery of the dressing 10 and the opening 12. The dressing 10 of this embodiment is preferably made of a moisture reactive material such as a hydrocolloid material although nearly any water reactive material including various hydrophilic or similar materials may be used. Additionally, the hydrocolloid material may include an antimicrobial or antibacterial material therein, such as a silver compound or a chlorhexidine gluconate compound to further reduce the incidence of exit site or catheter tract infections.

Figure 1:
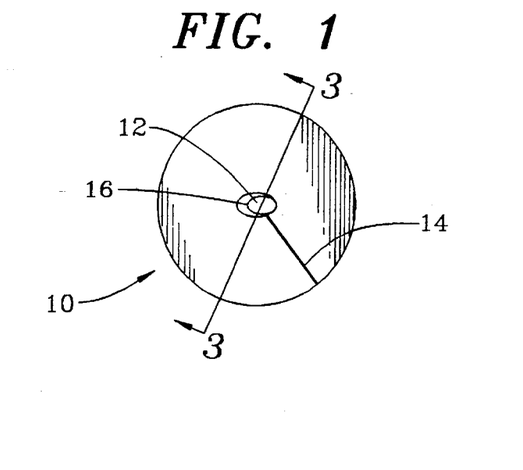
FIG. 1 is a top perspective view of one preferred form of the dressing of the present invention.

In the present intended use of this invention, the dressing preferably includes moisture reactive material therein which will draw moisture such as wound exudate from the exit site and which is also preferably nonreactive with the skin of the patient. The opening 12 is shown as a generally oval shaped opening although nearly any shape of opening may be used.

Figure 2:
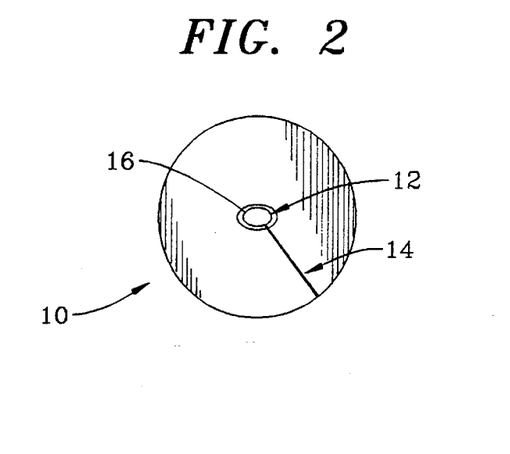
FIG. 2 is a bottom perspective view of the dressing of FIG. 1.
Figure 3:
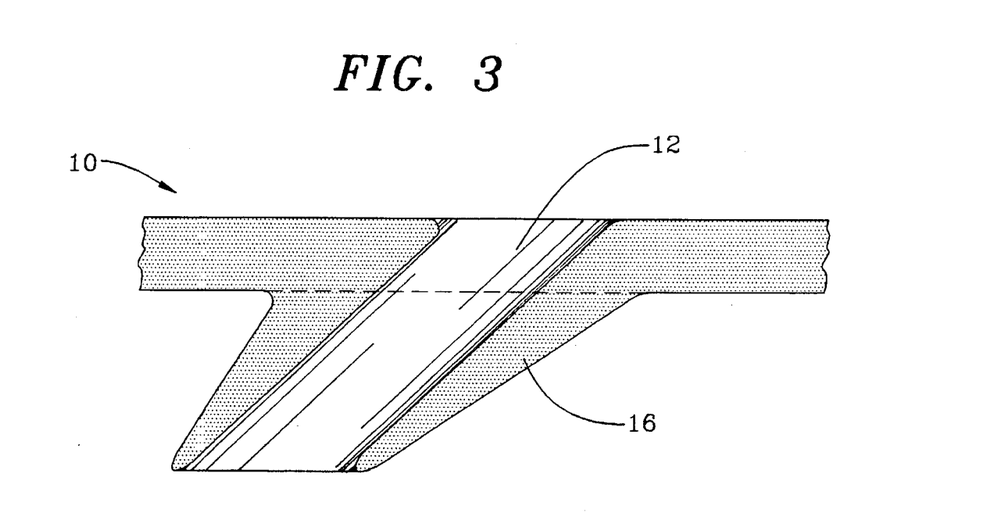
FIG. 3 is a cross sectional view of the dressing of FIG. 1 taken generally along lines 3—3 of FIG. 1.
Figure 4:
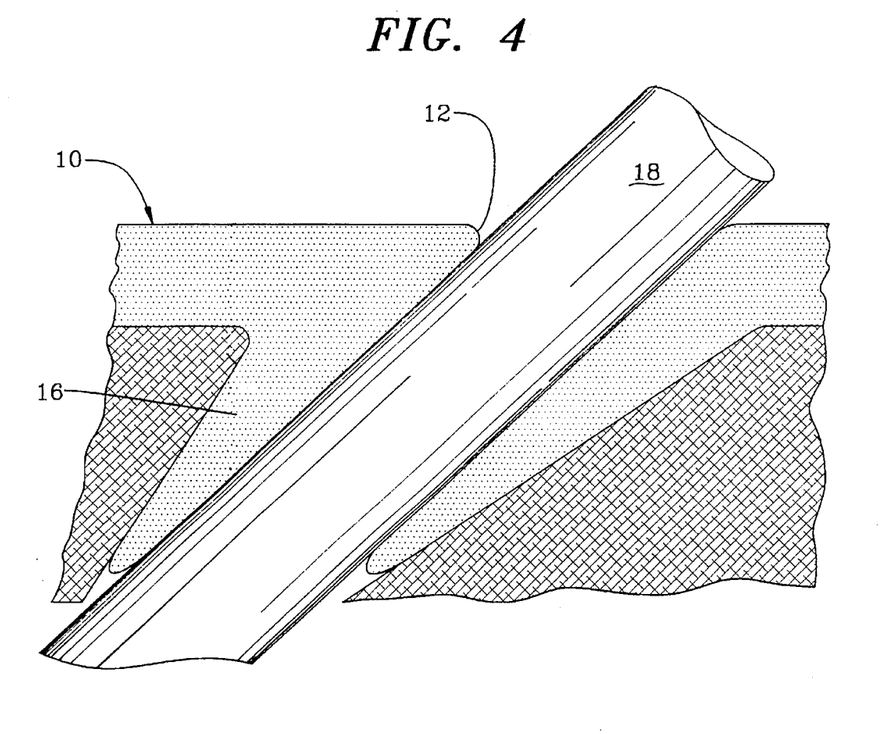
FIG. 4 is a cross sectional view of the dressing of FIG. 1 taken generally along lines 3—3 of FIG. 1 showing the dressing of the present embodiment with a catheter inserted therein and in place on the skin of the patient.

The shape of the opening is primarily dependent on the size and shape of the catheter 18 as well as the desired angle of insertion of the catheter into the patient. FIGS. 2, 3 and 4 also show the ridge-like lip surface or dressing lip 16 which extends downwardly from the bottom surface of the dressing 10 and which generally surrounds the circumference of the opening 12. The width or thickness of the dressing lip 16 preferably decreases from a location adjacent to the bottom surface of the dressing 10 to the bottom-most portion of the dressing lip 16 so that the insertion of the dressing 10 onto the catheter 18 and through the opening 12 is relatively easy. Additionally, the dressing lip 16 may easily be inserted into the catheter tract and around the exit site without having to expand or stretch the tissue around the exit site. In a preferred form of this embodiment, the dressing lip 16 is oriented at a preferred angle of about 5 to 90 degrees with respect to the bottom surface of the dressing to allow the catheter 18 to pass therethrough without altering currently used catheter positioning and insertion techniques. Additionally, the width and length of the dressing lip may be varied according to the intended use of the dressing. For example, in a form of the present embodiment shown in FIG. 3, the length of the dressing lip is preferably longer than the thickness of the dressing lip and more preferably approximately twice as long as the thickness of the dressing 10 and, in a more preferred form of this embodiment, the thickness of the dressing 10 may be between about 0.5 mm and 15 mm thick and the dressing lip 16 may be between about 1 mm and 10 mm long. As described above, the respective dimensions for the thickness of the dressing 10 and the dressing lip 16 are illustrative only and may be varied depending on the intended use of the dressing 10 and the size and shape of the catheter 18. For example, in one dressing designed for use with a Tenckhoff type of peritoneal catheter having an outer diameter of about 4.9 mm, the preferred thickness of the dressing is about 2.5 mm and the length of the dressing lip 16 is about 1.23 mm. In the dressing formed for use with this catheter, the dressing lip 16 is oriented at an angle of about 55 degrees with respect to the bottom surface of the dressing 10 and the opening is generally oval shaped with dimensions of about 4.5 mm and 6.0 mm respectively. The dressing 10 of this example, has a preferred diameter of approximately 31 mm.

In use, the dressing 10 is placed around the catheter 18 after the catheter 18 is inserted into the patient. Therefore, once the catheter 18 is placed in the patient, the dressing 10 is removed from the packaging and the portion of the dressing 10 adjacent to the slit 14 is grasped to separate the dressing 10 along the slit 14. The catheter 18 is then placed through the slit 14 until the shaft of the catheter 18 is positioned in the opening 12. The dressing 10 is then slid down the shaft of the catheter 18 until the bottom surface of the dressing 10 is adjacent to the skin of the patient and the dressing lip 16 is in the catheter tract and around the exit site as shown in FIG. 4. If desired, the edges of the dressing 10 may then be secured to the skin of the patient using a gauze tape or other type of adhesive material or the hydrocolloid material may be coated with an adhesive type material along at least a portion thereof to increase the adherence of the dressing to the skin of the patient. Alternately, the dressing 10 may be positioned on the shaft of the catheter 18 at the approximate desired position prior to final positioning of the catheter 18 in the patient so that the dressing 10 and catheter 18 may be moved together into the final inserted position as shown in FIG. 4.

Figure 5:
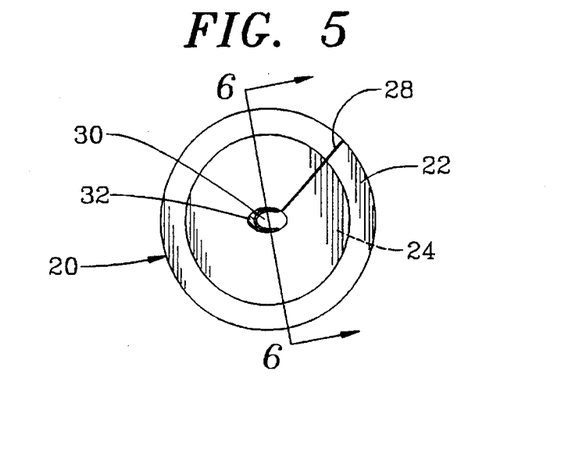
FIG. 5 is a top perspective view of an alternate preferred form of the dressing of the present invention.
Figure 6:
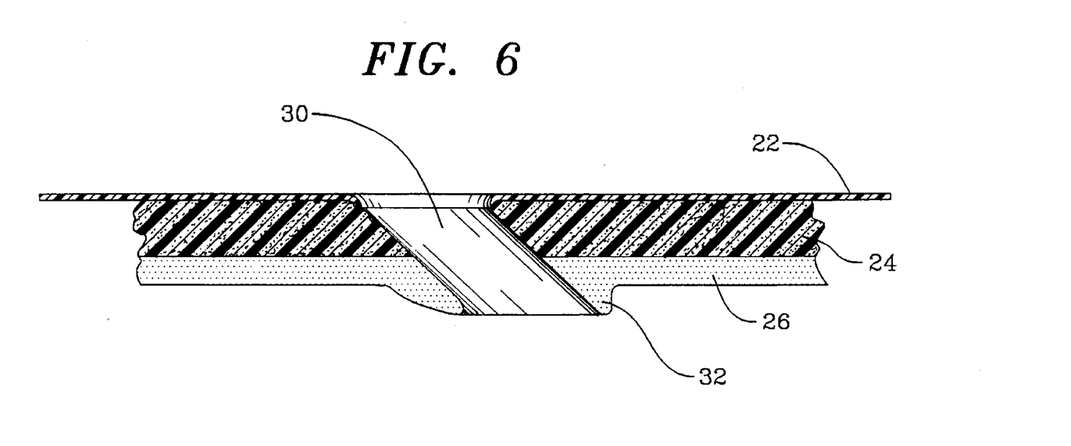
FIG. 6 is a cross sectional view of the dressing of FIG. 5 taken generally along lines 6—6 of FIG. 5.

FIGS. 5 and 6 illustrate a further preferred embodiment of the present invention. In this embodiment, the dressing 20 preferably includes three layers of different materials. The top layer is preferably formed by a film-like layer 22 which is made from a flexible material such as a polyurethane transparent film. The film-like layer 22 is preferably a one-way moisture permeable barrier which allows moisture from the wound to evaporate while not allowing the dressing 20 to become saturated with water if the clinician or patient gets the dressing 20 wet. Additionally, the film-like layer 22 is permeable to oxygen but impermeable to bacteria. The middle layer of the dressing 20 may be a foam-like layer 24 which provides greater medical integrity to the dressing 20 to allow for the easier handling of the dressing 20 during placement and removal. The foam layer 24 may be formed of nearly any nonreactive material. The bottom layer of the dressing 20 is preferably a hydrocolloid layer 26 although this layer may be formed of nearly any moisture reactive or hydrophilic material as described above. With the dressing 20 of this embodiment, the film-like layer 22 may be larger or have a greater diameter than the foam layer 24 and/or the hydrocolloid layer 26 as shown in FIGS. 5 and 6, so that the film-like layer 22 overlays one or both of the remaining layers. This arrangement of the respective layers will allow the film-like layer 22 to adhere directly to the skin of the patient. The use of the dressing 20 of the present embodiment is similar to the use of the dressing 10 described above except that it is believed to be easier to separate along the slit 28 to allow for the positioning of the catheter into the opening 30, and it is also believed to be easier to position the dressing lip 32 into the catheter tract and around the exit site.

Figure 7:
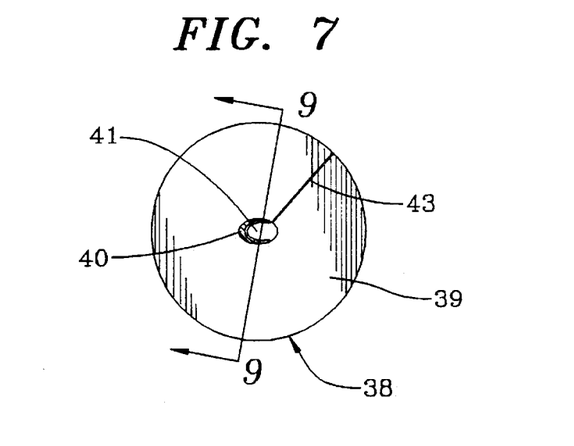
FIG. 7 is a top perspective of another alternate preferred form of the dressing of the present invention.
Figure 8:
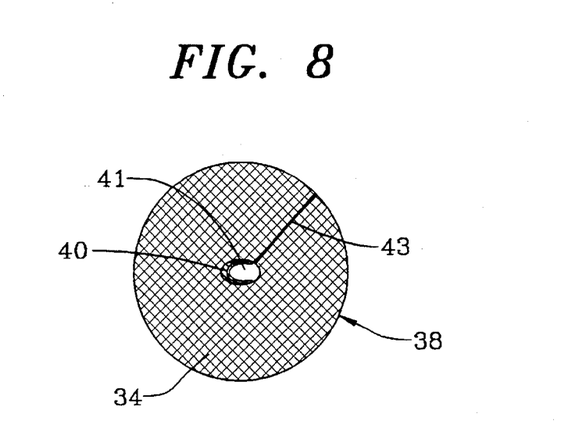
FIG. 8 is a bottom perspective view of the dressing of the embodiment shown in FIG. 7.
Figure 9:
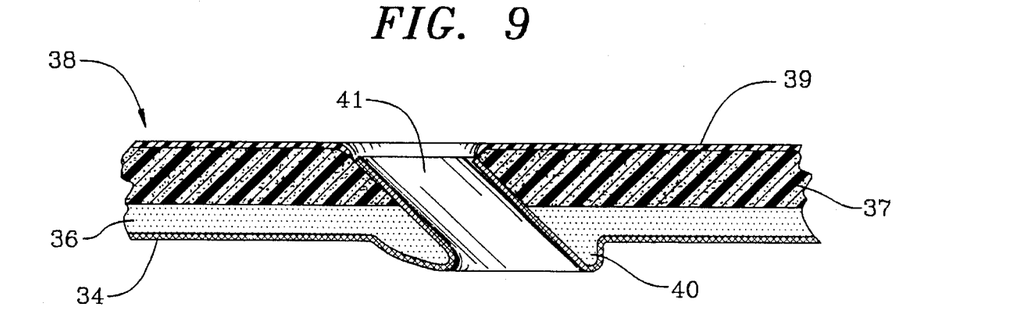
FIG. 9 is a cross sectional view of the embodiment of FIG. 7 taken generally along lines 9—9 of FIG. 7.

FIGS. 7–9 illustrate a further preferred embodiment of the present invention. In this embodiment, a mesh layer 34 of a preferably non-woven and non-reactive mesh-like material such as a polyethylene or polypropylene material is added to the bottom surface of the hydrocolloid layer 36 of the dressing 38 and may include a foam layer 37 and a film-like layer 39 as described above. The mesh layer 34 preferably has an open area which is preferably in the range of between about 20 to 60 percent to limit the tackiness of the dressing 38 and control the amount of hydrocolloid material which can seep through the openings of the mesh layer 34 and onto the skin of the patient or into the catheter tract. As shown in FIG. 9, the mesh layer 34 preferably extends along the dressing lip 40 and may also extend into the opening 41 of the dressing 38 to reduce the amount of hydrocolloid material which remains around the exit site and on the shaft of the catheter after removal of the dressing 38 while retaining the ability of the hydrocolloid material to draw the wound exudate from the skin and exit site.

In the embodiment shown in FIGS. 7–9, the mesh layer 34 surrounds the dressing lip 40 so that as the dressing 38 is removed from the skin of the patient by lifting the portions of the dressing 38 which are adjacent to the slit 43, the mesh layer 34 will pull the majority of the hydrocolloid material from the skin of the patient. Therefore it is believed that the dressing 38 of this embodiment will leave less hydrocolloid material on the skin of the patient or in the catheter tract than with the embodiments described above. In an alternate form of this embodiment (not shown), the dressing lip 40 may be eliminated and the mesh layer 34 may extend along the bottom surface of the hydrocolloid material to a location adjacent to or along the opening 41.

Figure 10:
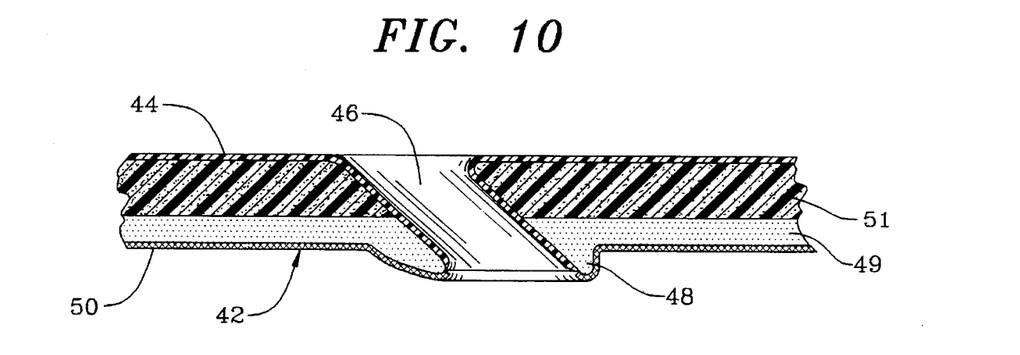
FIG. 10 is a cross sectional view of an alternate preferred embodiment of the present invention showing the film-like layer extending into the opening of the dressing rather than the mesh layer extending into the opening as shown and described for the embodiment shown in FIGS. 7-9.

FIG. 10 illustrates a further alternate embodiment of the present invention and is similar to the embodiment shown in FIGS. 7–9 as described above. On the cross-sectional view of the dressing 42 shown in FIG. 10, the film-like layer 44 extends from the top surface of the dressing 42 into the opening 46 and along the inner surface of the dressing lip 48.

The positioning of the film-like layer 44 along the inner surface of the dressing lip 48 allows the film-like layer 44 to contact the shaft of the catheter after placement of the dressing 42 on the skin of the patient so that it will be less likely that the clinician or patient will have to remove hydrocolloid residue from the shaft of the catheter after each dressing change. As shown in FIG. 10, the mesh layer 50 preferably extends along the bottom surface of the dressing 42 and the outer surface of the dressing lip 48 so that wound exudate, bacteria or other debris on the skin of the patient and in the catheter tract will be absorbed by the hydrocolloid material. The foam layer 51 is preferably positioned between the hydrocolloid layer 49 and the film-like layer 44.

Figure 11:
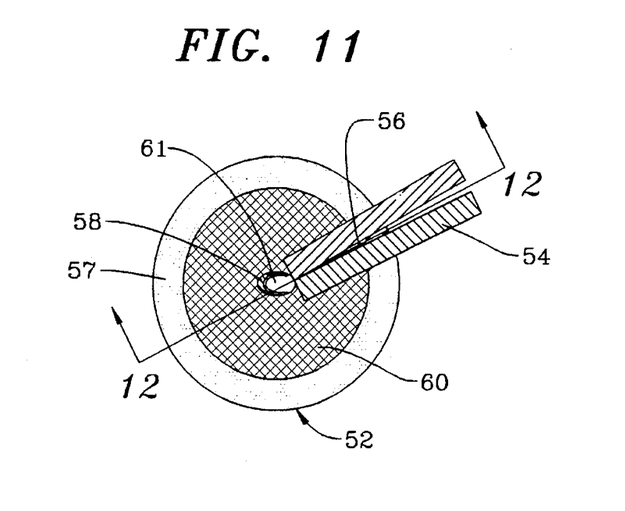
FIG. 11 is a bottom perspective view of yet another alternate preferred form of the present invention.
Figure 12:
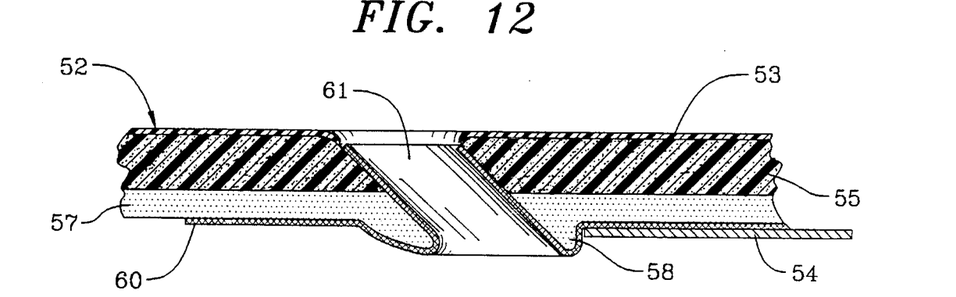
FIG. 12 is a cross sectional view of the embodiment shown in FIG. 11 taken generally along lines 12—12 of FIG. 11.

FIGS. 11 and 12 illustrate yet another preferred embodiment of the present invention. As with the embodiments described above, the present embodiment preferably includes a film-like layer 53, a foam layer 55, a hydrocolloid layer 57 and a mesh layer 60 as well as an opening 61. As shown in FIG. 12, the mesh layer of this embodiment may extend along the opening 61 such that the mesh layer is positioned adjacent to the percutaneous device (not shown) in use. In this embodiment, the dressing 52 also includes a pair of tab members 54 oriented along the slit 56 of the dressing 52 to assist in the positioning of the dressing 52 around the shaft of the percutaneous device and also to provide a surface which may easily be grasped to remove the dressing 52 from the skin of the patient. The tab members 54 are preferably made of a medical grade adhesive tape although a polyethylene or polypropylene similar to that which is used in the mesh layer 60 of this embodiment may also be acceptable with or without an adhesive material thereon. The tab members 54 preferably extend beyond the periphery of the dressing 52 to provide a surface which may be easily grasped when it is necessary to change the dressing 52. Additionally, the tab members 54 assist in separating the hydrocolloid material along the slit 56 during removal of the dressing 52 from the skin of the patient. The fusing of the edges of the dressing lip 58 is believed to be desirable so that a tract for the migration of bacteria into the exit site is not created along the tab members 54 or slit 56 and the physical barrier along the catheter and the skin of the patient is maintained. When it is necessary to change the dressing 52, the clinician or patient may grasp the outer portions of the tab members 54 and pull the tab members 54 away from each other and gradually towards the catheter to peel the dressing 52 away from the skin of the patient and away from the percutaneous device or catheter. As the tab members 54 are lifted, the mesh layer 60 is also lifted so that the overall majority of the hydrocolloid layer 57 is likewise lifted from the exit site and the shaft of the catheter.

Finally, FIGS. 11 and 12 illustrate the hydrocolloid layer 57 having a greater diameter than the mesh layer 60 such that the hydrocolloid layer 57 is in direct contact with the skin of the patient in an area that is easily cleaned and is spaced apart from the exit site as described more fully with respect to the following embodiment.

Figure 13:
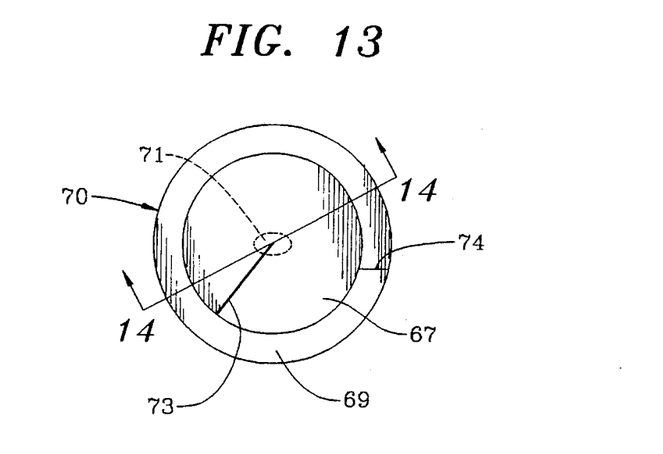
FIG. 13 is a bottom perspective view of yet another alternate preferred form of the present invention.
Figure 14:
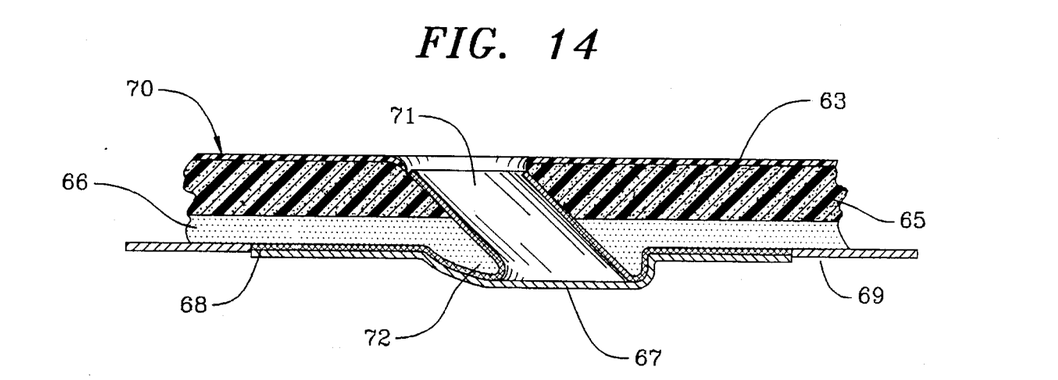
FIG. 14 is a cross sectional view of the embodiment shown in FIG. 13 taken generally along lines 14—14 of FIG. 13.

FIGS. 13 and 14 illustrate yet another preferred embodiment of the present invention which includes many of the features described above including a film-like layer 63, a foam layer 65 and an opening 71, as well as, a hydrocolloid layer 66 which is larger than the mesh layer 68 so that the periphery of the hydrocolloid layer 66 is exposed directly to the skin of the patient. It is believed that the presence of the exposed hydrocolloid layer 66 around the periphery of the dressing 70 creates an area around the circumference of the dressing which has a higher tack than the portion of the hydrocolloid layer 66 that has the mesh layer 68 therein so that the dressing 70 of this embodiment will stick to the skin of the patient better than in one or more of the embodiments described above. Additionally, FIGS. 13 and 14 illustrate the use of a pair of removable liner papers or protective layers 67 and 69 such that the first protective layer 67 along the mesh layer 68 may be removed as the dressing is initially placed around the percutaneous device and then the second protective layer 69 may be removed to finally secure the dressing in position on the skin of the patient. As shown in FIG. 13, each protective layer preferably has a slit 73 and 74 therein and it is also preferred that the first protective layer extend around at least a portion of the dressing lip 72 to protect the dressing lip 72 during transport and initial handling. In the present embodiment, the dressing 70 is shown as including a mesh layer 68 along the entire interior and exterior surfaces of the dressing lip 72 so that the hydrocolloid material is readily removable from the exit site and the shaft of the catheter.

Figure 15:
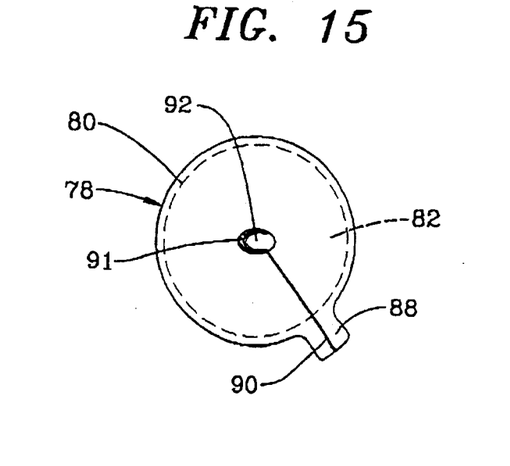
FIG. 15 is a top perspective view of a further preferred form of the present invention.
Figure 16:
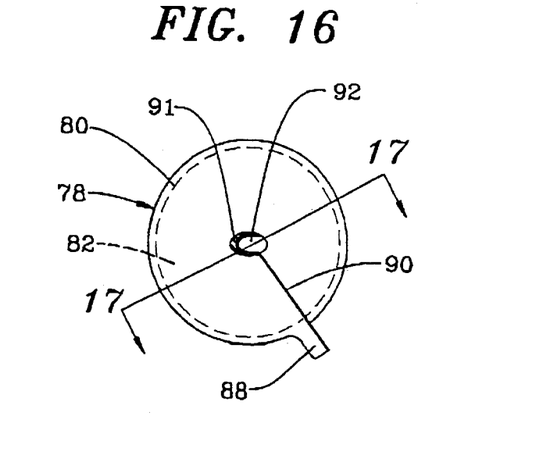
FIG. 16 is a top perspective view of a further preferred form of the present invention.
Figure 17:
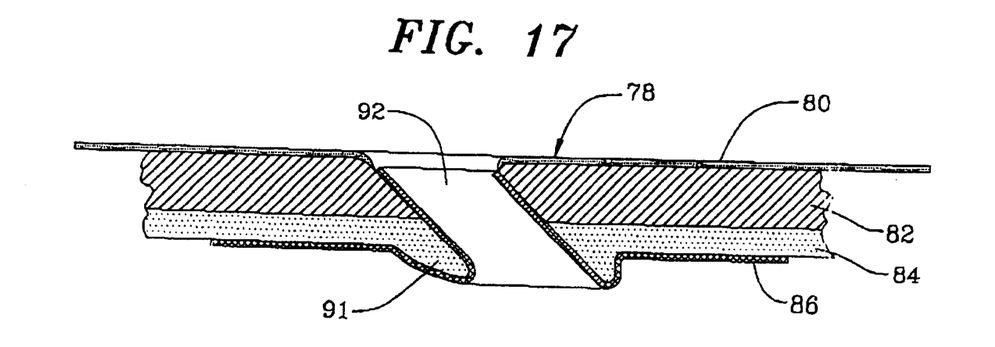
FIG. 17 is a cross sectional view of the embodiment shown in FIG. 16 taken generally along lines 17—17 of FIG. 16.

FIGS. 15, 16 and 17 illustrate further preferred embodiments of the dressing 78 of the present invention which includes many of the features described above as well as a film layer 80 and/or foam layer 82 which is larger than the hydrocolloid layer 84 and/or the mesh layer 86 so that the periphery of at least the film layer 80 is exposed directly to the skin of the patient and provides a convenient surface to hold or grasp when applying or removing the dressing as described more fully above. As shown in FIGS. 15, 16 and 17, at least the film layer 80 includes a tab-like portion thereon which extends from the remainder of the dressing. This tab extension 88 may include a slit 90 therein (FIG. 15) or be adjacent thereto (FIG. 16). As with the embodiments described above, the slit 90 preferably extends between the periphery of the dressing and the dressing lip 91 of the opening 92. Additionally, the tab extension 88 in this embodiment may be formed to include one or two pieces of elongate material that extend along the length of the slit 90. Alternately, the elongate material may extend along the slit 90 for the length of the tab extension 88. The tab extension 88 may also be formed with the adhesive surfaces facing the skin of the patient so that the portion of the dressing 78 adjacent to the slit 90 is applied directly to the skin of the patient to allow the clinician to ensure that the slit 90 remains closed when the dressing 78 is applied to the skin of the patient. When it is necessary to change the dressing 78, the clinician may grasp the outer portions of the tab extension 88 and pull the tab extension 88 from the skin of the patient or away from each other. The clinician may then pull the portions of the dressing 78 gradually towards the catheter to peel the dressing 78 away from the skin of the patient and away from the catheter. As the tab extension 88 is lifted, the hydrocolloid layer 84 and the mesh layer 86 are also lifted so that the overall majority of the dressing 78 is lifted and removed from the exit site and the shaft of the catheter.

While the foregoing is illustrative of various presently preferred forms of the present invention, it is anticipated that a person skilled in the art may, after reviewing the foregoing, conceive of variations of the present invention which are not explicitly described above but which are still within the scope of the present invention as defined by the following claims.

What is claimed is:

1. A protective member for use with a percutaneous device which extends from the skin of the patient, the protective member comprising;

a flexible dressing having a first portion formed as generally planar member having at least a top surface and a bottom surface wherein said bottom surface is formed to generally conform to the top skin surface of the patient; and a second portion formed of a moisture reactive material and said second portion is associated with said dressing and includes a tapered downwardly extending member which is sized to extend from said bottom surface of said first portion to a location below the top skin surface of the patient in use.

2. The protective member of claim 1 wherein said bottom surface includes a hydrophilic material therein.

3. The protective member of claim 1 wherein said second portion is oriented at an angle of less than ninety degrees with respect to said first portion.

4. The protective member of claim 1 wherein said second portion includes a hydrophilic material therein.

5. The protective member of claim 1 wherein said top surface of said first portion includes a flexible film-like protective material therein and said film-like layer allows the passage of moisture in one direction therethrough while inhibiting the passage of moisture therethrough in another direction.

6. The protective member of claim 1 wherein said dressing includes an opening therein which is sized to receive at least a portion of a percutaneous device therein and said second portion is oriented generally adjacent to at least a portion of said opening.

7. The protective member of claim 6 wherein said second portion surrounds the periphery of said opening and is oriented to extend along at least a portion of the percutaneous device.

8. The protective member of claim 6 wherein said dressing includes a periphery and said opening therein which is sized to receive at least a portion of a blood access device therein and said dressing further includes a slit therein which extends between said periphery of said dressing and said opening.

9. The protective member of claim 8 wherein one or more tab members extend between said periphery of said dressing and said opening.

10. The protective member of claim 8 wherein one or more tab members are positioned on said dressing.

11. The protective member of claim 10 wherein said one or more tab members are oriented along said slit and extend between said periphery of said dressing and said opening.

12. A protective member for use with a percutaneous device which extends from the top surface of the skin of the patient, the protective member comprising;

a flexible dressing having a first portion formed as a generally planar member having at least a top surface and a bottom surface wherein said bottom surface is formed to generally conform to the top skin surface of the patient;

an opening formed in said dressing wherein said opening is sized to receive at least a portion of a percutaneous device therein;

a second portion formed of a moisture reactive material and said second portion is associated with said dressing and includes a downwardly extending member which is sized to extend from said bottom surface of said first portion to a location below the top skin surface of the patient in use and at least a portion thereof is oriented along at least a portion of said opening.

13. The protective member of claim 12 wherein at least a portion of said dressing is formed of a hydrophilic material.

14. The protective member of claim 12 wherein said second portion is formed of a hydrophilic material.

15. The protective member of claim 12 wherein said dressing includes a periphery thereon and a slit extends between said periphery thereof and said opening.

16. The protective member of claim 12 wherein said dressing includes a film-like layer therein.

17. The protective member of claim 16 wherein said film-like layer allows the passage of moisture in one direction while inhibiting the passage of moisture therethrough in another direction.

18. A protective member for use with a percutaneous device which extends from the top surface of the skin of the patient, the protective member comprising;
- a dressing having a first portion formed as generally planar member having at least a top surface with a film-like layer thereon and a bottom surface which includes a moisture reactive material therein and wherein said bottom surface is flexible and is formed to generally conform to the top skin surface of the patient;
- an opening formed in said dressing wherein said opening is sized to receive at least a portion of a percutaneous device therein; and
- a second portion formed of a moisture reactive material and said second portion is associated with said dressing such that a downwardly extending member is formed by said second portion which is sized to extend from said bottom surface of said first portion to a location below the top skin surface of the patient in use and at least a portion thereof is generally tapered and oriented along at least a portion of said opening to extend below the top surface of the skin of the patient and along at least a portion of the percutaneous device in use.

19. The protective member of claim 18 wherein said second portion is oriented at an angle of less than ninety degrees with respect to said first portion.

20. The protective member of claim 18 wherein said film-like layer includes a slit therein which extends along at least said first portion.

21. The protective member of claim 18 wherein said film-like layer extends along at least a portion of said second portion and is generally adjacent to the percutaneous device in use.

22. The protective member of claim 18 wherein said second portion is oriented generally along said opening and extends generally from a location generally adjacent to said bottom surface of said first portion to an apex which is positioned below the top surface of the skin of the patient in use.

23. The protective member of claim 18 wherein said first portion of said dressing has a first thickness and said second portion has a lengthwise dimension and said lengthwise dimension of said second portion is greater than said thickness of said dressing.

24. The protective member of claim 18 wherein said dressing has an outer periphery and includes a slit therein which extends between said periphery of said dressing and said opening.

25. The protective member of claim 18 wherein said film-like layer extends along at least said first portion and a portion of said second portion.

26. The protective member of claim 25 wherein said film-like layer extends laterally beyond the top said surface of said first portion.

27. A protective member for use with a percutaneous device which extends from the top surface of the skin of the patient, the protective member comprising;
- a dressing having a first portion formed as generally planar member having at least a top surface with a film-like layer thereon and a bottom surface which includes a moisture reactive material thereon and wherein said bottom surface is flexible and is formed to generally conform to the top skin surface of the patient;
- a opening formed in said dressing wherein said opening is sized to receive at least a portion of a percutaneous device therein;
- a second portion oriented generally along the periphery of said opening and extending downwardly from said bottom surface of said first portion; and
- a further layer positioned generally between said top surface and said bottom surface of said first portion wherein said further layer is formed of a foam layer and said foam layer extends along at least a portion of said moisture reactive material.

28. The protective member of claim 27 wherein said moisture reactive material includes a hydrophilic material which extends along a greater portion of said bottom surface of said dressing than said foam layer.

29. The protective member of claim 27 wherein said dressing includes said second portion formed of a moisture reactive material and said second portion is associated with said dressing such that a downwardly extending member is formed by said second portion which is sized to extend from said bottom surface of said first portion to a location below the top skin surface of the patient in use and at least a portion of said opening in said dressing to extend below the top surface of the skin of the patient and along at least a portion of the percutaneous device in use.

30. The protective member of claim 27 wherein said dressing includes a tab-like extension thereon which extends generally from the periphery of said dressing to assist in grasping a portion of said dressing to facilitate the application or removal of said dressing from the patient.

31. The protective member of claim 27 wherein said dressing includes said opening extending therethrough and a film layer which extends along said opening such that said film layer extends between said foam layer and said moisture reactive and the percutaneous device.

32. The protective member of claim 27 wherein said dressing includes said opening extending therethrough and said foam layer extends along said opening such that said foam layer extends between said and a film-like layer and a portion of said film-like layer is generally adjacent to the percutaneous device in use.

33. The protective member of claim 27 wherein said moisture reactive material includes an antimicrobial material therein.

* * * * *